United States Patent [19]

Lew et al.

[11] Patent Number: 5,653,973

[45] Date of Patent: Aug. 5, 1997

[54] LEPIDOPTERA BAIT

[75] Inventors: Chel W. Lew, San Antonio, Tex.; Keith Branly, Brandon, Fla.; Jesse Gaytan, Valdosta, Ga.; Osborn Jones Turner, Lakeland, Fla.

[73] Assignee: Micro Flo Company, Mulberry, Fla.

[21] Appl. No.: 699,624

[22] Filed: Aug. 16, 1996

[51] Int. Cl.$^6$ .......... A01N 25/08; A01N 25/20; A01N 25/22; A01N 33/04

[52] U.S. Cl. .......... 424/84; 424/409; 424/410; 424/484; 424/489; 424/601; 424/605; 424/606; 424/660; 424/677; 424/709; 424/711; 424/715; 424/718; 424/723; 426/1; 514/65; 514/120; 514/122; 514/431; 514/521; 514/531; 514/671

[58] Field of Search .......... 424/84, 409, 410, 424/484, 489, 601, 605, 606, 660, 677, 709, 711, 715, 718, 723, 970; 426/1; 514/65, 120, 122, 431, 521, 531, 671; 43/113

[56] References Cited

U.S. PATENT DOCUMENTS

| 2,580,414 | 1/1952 | Duffey | 424/408 |
|---|---|---|---|
| 3,091,567 | 5/1963 | Warzburg et al. | 424/418 |
| 3,515,070 | 6/1970 | Cutler et al. | 102/513 |
| 3,576,987 | 5/1971 | Voight et al. | 362/34 |
| 3,729,425 | 4/1973 | Heller et al. | 252/700 |
| 4,670,250 | 6/1987 | Baker | 424/419 |
| 4,918,856 | 4/1990 | Olive et al. | 43/113 |
| 4,983,390 | 1/1991 | Levy | 424/404 |
| 5,073,295 | 12/1991 | Bruttel et al. | 252/301.19 |

OTHER PUBLICATIONS

Caplus Abstract Accession No. 1979:520660; Abstracting, Noguchi et al., "Sex Pheromone of the Tea Tortrix moth: Isolation and Identification," Appl. Entomol. Zool., vol. 14(2), 1979, pp. 225–228.

Evaluation of Feeding Stimulants for Adust Helicoverpa Zea, J.D. Lopez, Jr., T.N. Shaver and P.D. Lingren, (1994).

*Primary Examiner*—John Pak
*Attorney, Agent, or Firm*—Banner & Witcoff, Ltd.

[57] ABSTRACT

Baits useful for controlling lepidoptera populations is made with (a) a diet component for lepidoptera; (b) a toxicant; (c) a chemiluminescent, visual attractant and (d) an encapsulating agent that will allow moisture to permeate and form an external condensate of said diet and said toxicant. The diet, toxicant, and chemiluminescent visual attractant can be used in the same bait particle in a homogeneous or layered structure. Alternatively, the diet/toxicant may be used with a first encapsulating agent in a first bait particle with the chemiluminescent, visual attractant encapsulated in a second bait particle and distributed among the diet/toxicant bait particles.

20 Claims, No Drawings

LEPIDOPTERA BAIT

FIELD OF THE INVENTION

Lepidoptera baits include encapsulated diet with a toxicant that is released when the humidity level increases (e.g., at night) but ceases when the humidity level drops (e.g., daytime).

BACKGROUND OF THE TECHNOLOGY

Moths and related forms of lepidoptera continue to be pests that are difficult to control with selective baits. Traditional control measures typically include aerial sprays over plants located in a designated geographical area during the larval stage of the target pest. The larvae die as they consume the insecticide-bearing foliage and/or are contacted by the spray. Unfortunately, there are concerns over the impact of such area treatments on nontarget insects as well as humans within or entering the area.

The art has proposed a number of lepidoptera baits that include a diet component and toxicants in a wide variety of formulations and physical forms. The diet generally is a sugar. See, e.g., U.S. Pat. Nos. 5,424,410 and 4,515,813. These baits tend to rely on the scent of the diet component and the lepidoptera's ability to sense the diet from a distance. Such scents can be subject to reduced effectiveness due to prevailing or unforseen wind currents that carry the diet scent away from the baited area thereby reducing the effectiveness of the bait. Indeed, it would be useful to have a bait that attracted the target lepidoptera to the bait with a means that did not rely on olfactory sensing of the diet component.

SUMMARY OF THE INVENTION

It is an object of the invention to provide a composition and use thereof for controlling lepidoptera populations.

It is also an object of the invention to provide a lepidoptera bait and method of use that provides a visual attractant that will draw target lepidoptera to the bait without vulnerability to wind currents.

In accordance with these and other objects of the invention that will become apparent from the description herein, a bait according to the invention is useful for controlling lepidoptera populations, is in the form of discrete particulates, and includes:

(a) a diet component for lepidoptera;

(b) a toxicant;

(c) a chemiluminescent visual attractant; and (d) an encapsulating agent that will permit moisture to permeate the encapsulating agent and allow said diet/toxicant components to form an external condensate for consumption by the target lepidoptera. The diet and toxicant may be used in the same physical particle as the chemiluminescent visual attractant, or the diet and toxicant components may be dispersed in the target area in a bait particle that is physically separate from a second bait particle containing the chemiluminescent visual attractant.

The present composition includes an outer shell that will release the encapsulated toxicant and lepidoptera diet when the ambient humidity level increases, such as in the evening and through the night when lepidoptera are actively feeding. The light emitting attractant that radiates a source of light at wave lengths visible and attractive to lepidoptera when feeding at night as the diet/toxicant condensate is formed. The encapsulating shell material reduces or terminates release as the humidity level drops, such as during the day. The result is a bait that targets lepidoptera through their diet and daily feeding behavior thereby reducing the impact on nontarget organisms and human exposure to treated areas.

DETAILED DESCRIPTION OF THE INVENTION

The lepidoptera bait of the invention includes lepidoptera diet component and a toxicant in an encapsulating shell or matrix therefore in conjunction with a light emitting attractant for visually attracting lepidoptera to the bait. The chemiluminescent visual attractant may be in the same physical particle composition or may be used in a separate, discrete particle that is physically admixed with the diet/toxicant bait particle. The encapsulating shell or matrix material controls the release of the diet and toxicant to direct the effectiveness of the bait to the feeding behavior of target lepidoptera.

Diet

The diet component is generally characterized as a food source for the target. For lepidoptera, exemplary diet component can be selected from one or more of those water soluble lepidoptera foods, including honey, sugars (fructose, sucrose, glucose, etc.), corn syrup solids, and maltodextrin.

Toxicant

Toxicants are agents that will kill or sterilize the target upon consumption thereof. Insecticides useful for the invention are those effective to control the target populations by killing or sterilizing the target insect. Generally, an amount within the range of 0.01–99 wt %, preferably 0.1–50 wt %, even more preferably an amount within the range of 0.01–10 wt %. A particularly preferred amount of insecticide is within the range from about 0.1–5 wt % based on the total weight of the bait.

Insecticides useful in the invention are materials and biological agents that control lepidoptera populations through lethal ingestion, sterilization, or other interference with the lepidoptera life cycle. Exemplary insecticides include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the digestive tract tissue including fluorine compounds (cryolite), zinc, and mercury; nicotine; rotenone; neem oil or azadiractin; natural or synthetic pyrethrins (permethrin, cypermethrin); petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); and microbials (e.g., *Bacillus thuringiensis* and entomopathic viruses). Preferred insecticides include malathion, permethrin, cypermethrin, endosulfan, and acephate.

Visual Attractant

A particularly useful component of the present bait is a chemiluminescent visual attractant that will emit light as a visual attractant for lepidoptera at night. Suitable visual attractants are chemiluminescent agents that produce light through one or more chemical reactions when the relevant chemical components are brought into contact with oxygen, such as when the encapsulating agent allows moisture to permeate.

Preferred visual attractants are made from an oxygen-sensitive component A and a salt B that complexes with the oxidized byproducts of component A to extend the duration and intensity of the chemiluminescence. Oxygen-sensitive component A can be made from the tetrakis (disubstituted amino) ethylene such as tetrakis (dimethyl amino) ethylene, known by its acronym TMAE.

Salt B can be made from lithium halides (chloride is most preferred), sodium or potassium nitrate ($NaNO_3$ or $KNO_3$), sodium or potassium carbonate ($Na_2CO_3$ or $K_2CO_3$), sodium or potassium thiosulfate ($Na_2S_2O_3$ or $K_2S_2O_3$), sodium or potassium phosphate ($Na_3PO_4$ or $K_3PO_4$), sodium borate ($NaB_4O_7$), potassium sulfate ($K_2SO_4$), or potassium bromide (KBr).

The individual components used to generate chemiluminescence can be presented with the diet/toxicant in a number of ways. The first way is to intimately admix the components together in the same bait as the diet/toxicant component. The second is to individually encapsulate the chemiluminescent agent into discrete solids which are then either dispersed in the bait or dispensed as discrete particles along with diet/toxicant particles. The choice of particular dispersion schemes is well within the existing level of ordinary skill in this art and will depend on the characteristics of the specific chemiluminescent components used.

In general, the amount of light emitting agent that is used in the same physical particle as the diet/toxicant components will be within the range from about 10 wt % to about 80 wt %.

If used as discrete particles, the chemiluminescent agent or agents are encapsulated with a source of hydratable solids in the same type of encapsulating agents as those used for encapsulation of the diet/toxicant components. The hydratable solids may be the same as those used as the diet component in the diet/toxicant bait particle or the hydratable solids may be different. The hydratable solids serve the function of carrying the chemiluminescent agent or agents into contact with oxygen. It is oxygen that initiates the generation of light from reaction between or with the luminescing agent or agents. Useful hydation agents for encapsulation with chemiluminescent agents in discrete particles free of toxicant include fucose, fructose, sucrose, glucose, honey, corn syrup solids, maltodextrin, sorbose, ribose, maltose, raffinose, turanose, rhamnose, galactose, and melizotose.

Because of the attractant effects of these luminescing particles and the behavior of lepidoptera near food sources, fewer numbers of luminescing particles can be dispersed with the diet/toxicant bait particles in a treatment area. When dispersed as a discrete particle, the luminescing particles can be used in an amount within the range from about 0.1 wt % to about 100 wt %, preferably within the range from about 2–20 wt %.

Lepidoptera that can be controlled with the present bait and its method of use include: *Ephestia spp., Mamestra spp., Earias spp., Pectinophora spp., Ostrinia spp., Trichoplusia spp., Pieris spp., Laphygma spp., Agrotis spp., Amathes spp., Wiseana spp., Tryporyza spp., Diatraea spp., Sporganothis spp., Cydia spp., Archips spp., Plutella spp., Chilo spp., Heliothis spp.* (e.g., *Heliothis virescens* also known as "tobacco budworm", *Heliothis armigera* and *Heliocoverpa zea*), *Spodoptera spp.,* and *Tineola spp.*

Because the various light emitting chemiluminescent agents described above will emit light at different wavelengths, a simple screening test that is well within the existing level of ordinary skill in this art can be used to "fine tune" a bait to be particularly attractive toward a designated target species.

Encapsulating Agent

Useful encapsulating agents are those that form a solid at room temperature and will swell when the ambient humidity raises above about 35% relative humidity to allow the diet component to hydrate and form an external condensate or "sweat" of the diet/toxicant components on the surface of the bait particle. Consumption of the diet necessarily includes, therefore, simultaneous consumption of toxicant. This mechanism presents diet to the lepidoptera when the lepidoptera are most actively feeding (i.e., at night) and conserves the bait when the lepidoptera are less active (i.e., during the day).

Suitable encapsulating agents are characterized by one of the following:

(a) water insoluble but swellable in water (e.g., ethyl cellulose);

(b) water insoluble but alcohol soluble with poor water barrier properties (e.g., shellac);

(c) water insoluble but poor to fair in moisture barrier properties (e.g., fats, shellac, waxes, polyethylene glycols modified to be water insoluble, water resistant, or with minimum water solubility);

(d) insoluble in cold water (less than about 30° C.) but soluble in hot water (e.g., cellulose and cellulose derivative polymers such as methylcellulose, hydroxypropylcellulose, hydroxypropylmethylcellulose, and mixtures thereof);

(e) soluble in water or alcohol, and/or acetone or other ketones (e.g., hydroxypropylcellulose or ethylcellulose); or (f) soluble in water or alcohol and/or acetone or other ketones but insoluble while in solution with one or more water soluble salts (e.g., hydroxypropylcellulose and trisodium phosphate).

Exemplary encapsulating agents include shellac, polyethylene oxide, polyvinylpyrrolidine, polyethylene glycol modified to exhibit reduced water solubility characteristics, fats, waxes, low molecular weight polyethylene, and alcohol soluble polymers in an amount sufficient to fully encapsulate the diet/toxicant and/or chemiluminescent gents in a structurally sound particle.

Baits according to the invention using a cold water insoluble/hot water soluble encapsulation matrix have a matrix or outer shell material exhibiting a thermal gelation temperature within the range from about 90° F. (about 30° C.) to about 160° F. (about 72° C.). If made in the form of a layered bait, the outer shell should have a thickness sufficient to ensure coverage of the entire core surface area. Suitable thicknesses are greater than about 3µ thick, preferably about 3µ to about 50µ, and even more preferably about 10–20µ in thickness. These shell thicknesses will typically result in an outer shell weight of at least about 5 wt % of the entire microcapsule weight. The thickness and corresponding weight percentage of the shell may be increased to provide additional protection against rupture during handling.

The thermal gelation temperature of the encapsulating material is the temperature at which the shell polymers start to lose their water of hydration find become insoluble in water. The start of gelation is manifested by an increase in solution viscosity and is readily determined by conventional viscosity measurements. The solution viscosity continues to increase as the solution is held at a temperature above the material gelation temperature.

Certain additives and be added to the outer shell material to affect its gelation temperature and tailor the release of the food enhancing additive to the thermal handling sequence of the food product. For example, shell additives such as sorbitol and glycerine can depress the gelation temperature by about 10° F. to about 36° F., but other shell additives such as ethanol and propylene can increase the gelation temperature by up to about 45° F. Sucrose is one shell additive that can be used to either depress or elevate the gelation temperature depending on the amount used. Adding relatively low amount, about 5 wt %, can elevate the gelation temperature up to about 10° F. yet relatively larger amounts, about 20 wt %, can depress the gelation temperature by up to about 45° F. Table 1 lists the gelation temperatures for various cellulose polymers with various shell additives.

TABLE I

| Additive | Wt % | Gelation Temperature (°F.) | | |
|---|---|---|---|---|
| | | Methocel™ A15C | Methocel™ F15C | Methocel™ K4M |
| None | | 122 | 145 | 185 |
| MgCl$_2$ | 5 | 107 | 125 | 153 |
| sucrose | 5 | 124 | 151 | 183 |
| sucrose | 20 | 111 | 138 | 142 |
| sorbitol | 20 | 86 | 115 | 118 |
| glycerine | 20 | 93 | 140 | 149–158 |
| ethanol | 20 | 167 | 167 | 167 |
| propylene | 20 | 138 | 176 | 176 |

Methocel ® A15C is a methylcellulose gum at 1500 cP viscosity
Methocel ® F15C is a hydroxypropylmethylcellulose gum at 1500 cP viscosity
Methocel ® K4M is a hydroxypropylmethylcellulose gum at 4000 cP viscosity Importantly, the shell/encapsulating agent containing the diet component (or hydratable sugar component when used as a discrete chemiluminescent particle) will rehydrate as the ambient humidity level rises (such as at night during the Summer), swell or otherwise allow moisture to permeate through the encapsulating agent, and form a "sweat" or external condensate of the encapsulated diet. The luminescent glow from the chemiluminescent agents acts as a visual attractant to the area until the lepidoptera are sufficiently close to be attracted to the diet condensate. As the lepidoptera feed on the diet, they also ingest effective levels of toxicant. The adult lepidoptera population is thereby targeted and controlled without the need to indiscriminately spread toxicant over all plant surfaces in the treated area.

Optional ingredients for encapsulation in the shell or matrix material include clays and clay solids for enhanced absorption of encapsulated or dispersed components, coloring agents (e.g., dyes or pigments) for visual stimulation of target insects or identification of the bait particles during daylight, bioadhesive polymers for enhancing adhesion to foliage or other elevated surfaces (tree limbs or trunk sections, plant stalks, etc.), and gustatory stimulants that encourage feeding in the target lepidoptera population.

Bait Structure

The baits of the present invention are made in the form of discrete, particulate solids exhibiting either a layered, core-and-shell structure or a homogeneous distribution of dispersed components in an encapsulating matrix. The particular method and the conditions used during the manufacture will depend on the structure desired and the characteristics of the specific encapsulating component.

In general, layered baits are made by coextrusion of liquid or liquefied core and shell components through a concentric nozzle into a collection zone at conditions sufficient to harden the shell component and encapsulate the core material. The particular hardening mechanism will depend on the type of encapsulating material or materials that are used.

For meltable encapsulating agents, the encapsulating component is melted at temperatures that do not materially degrade the dispersed components (e.g., polyethylene glycol, waxes, fats, and low molecular weight polyethylene). Salt sensitive encapsulating agents are preferably formed into bait particles and collected in an aqueous bath containing the applicable salt for rendering the encapsulating agent insoluble in water. Alternatively, salt sensitive baits can be collected and dried in a starch bed for recovery. Alcohol soluble shell materials are dissolved in a suitable solvent alcohol, while hot water soluble/cold water insoluble encapsulating agents are formed into bait at the elevated temperature of solubility.

If a homogeneous particle structure is desired, the encapsulated components are mixed into the liquefied matrix material until thoroughly and uniformly dispersed, and the liquid mixture is formed into particles by any of the conventional methods for forming particles from a liquid mixture, e.g., spray drying, rotating disk, extrusion through a nozzle, granulation, marumerizer, or with a compacter. The selection of one of these specific methods will be apparent to those in the art upon evaluation of the applicable temperatures, viscosities (or lack thereof), and solidification characteristics of the bait material.

If a layered particle structure is desired, the core material is coextruded through the central nozzle of a set of concentric nozzles, the outer shell material passing through the outermost nozzle opening.

Regardless of the structure, the molten particle is ejected into the top of a cooling zone containing a cooling fluid for cooling and solidification. Preferably, the cooling zone has an upflowing stream of relatively cooler air that allows the bait particle to cool and solidify sufficiently by the time the particle reaches the bottom of the cooling zone that the particle retains a substantially spherical shape.

The bait particles can be made in a wide variety of sizes, the particular size desired being matched to the method of distribution within the target treatment area. If intended for application through conventional spraying equipment, a particle size is generally advisable that is sufficiently small for acceptable dispersion in the spray tank without thickening the liquid yet of a sufficiently large diameter to control drift away from the target treatment area the baits are desirably formed into a roughly spherical bait having a diameter of less than about 1000 μm. Preferably, 100% of the bait exhibits a particle size within the range from about 100 μm to about 600 μm. Particularly effective particle sizes are when 100% of the bait particles are within the range of about 300 μm to about 600 μm.

Dry granular baits, on the other hand, will generally exhibit a larger corresponding size within the range from about 800 μm to about 2000 μm. Within the range of about 600–800 μm, the baits can be used as either a sprayable bait or a dry granular bait depending on the cold water solubility of the binder employed.

Dry granular baits are desirable made by depositing a homogeneous mixture of corn germ, insecticide, and binder on corn cob grit. Alternatively, a plurality of <600 μm preformed baits, such as those dispersed by spraying, can be deposited on a grit carrier and held thereon with the same binder as in the bait or a different binder.

EXAMPLES

The compositions of encapsulated diet/toxicant in Table 2 were prepared as discrete particles. Each of these was tested for an ability to permit moisture to permeate at a relative humidity of about 35% and to form an external condensate containing the encapsulated diet and toxicant components. The technical grade of active ingredient contained the identified concentration of active ingredient in AROMATIC 150™ solvent (an aromatic hydrocarbon solvent available from Exxon Chemical) except for the following: examples 4 and 8 used isopropyl alcohol, ex. 13 used ethanol, and ex. 14 was with acetone.

Samples were prepared by making a homogeneous mixture of the diet, toxicant, and encapsulating material. The mixture was then formed into discrete particles of 75–212 µm by extruding the mixture through nozzles along the perimeter of a laboratory rotating disk device. The bottom of a free fall collection zone contained starch into which the particles were allowed to fall and collect. Particles were recovered by screening the starch. For each composition, 20 g. of each were prepared.

TABLE 2

| Example No. | Encapsulating Composition (Wt. %) |
| --- | --- |
| 1. | 20.0 Shellac |
|  | 79.5 Sucrose |
|  | 0.5 Cypermethrin (50.0% Tech) |
| 2. | 14.0 Ethylcellulose |
|  | 6.0 Hydroxypropylcellulose |
|  | 79.5 Powdered Fructose |
|  | 0.5 Cypermethrin (50.0% Tech.) |
| 3. | 50.0 Sterotex ™ HM (Fat) |
|  | 49.5 Sucrose |
|  | 0.5 Cypermethrin (50.0% Tech.) |
| 4. | 18.0 Polyethylene Glycol |
|  | 2.0 Monamid ™ S (Fatty Amides) |
|  | 79.5 Powdered Fructose |
|  | 0.5 Cypermethrin (50.0% Tech.) |
| 5. | 20.0 Shellac |
|  | 79.0 Sucrose |
|  | 1.0 Endosulfan (34.5% Tech.) |
| 6. | 14.0 Ethylcellulose |
|  | 6.0 Hydroxypropylcellulose |
|  | 79.0 Powdered Fructose |
|  | 1.0 Endosulfan (34.5% Tech.) |
| 7. | 50.0 Sterotex ™ HM (fat) |
|  | 49.0 Sucrose |
|  | 1.0 Endosulfan (34.5% Tech.) |
| 8. | 18.0 Polyethylene Glycol |
|  | 2.0 Monamid ™ S (Fatty Amides) |
|  | 79.0 Powdered Fructose |
|  | 1.0 Endosulfan (34.5% Tech.) |
| 9. | 20.0 Shellac |
|  | 79.0 Sucrose |
|  | 1.0 Malathion (57.0% Tech.) |
| 10. | 14.0 Ethylcellulose |
|  | 6.0 Hydroxypropylcellulose |
|  | 79.0 Powdered Fructose |
|  | 1.0 Malathion (57.0% Tech.) |
|  | 50.0 Sterotex ™ HM (fat) |
| 11. | 49.0 Sucrose |
|  | 1.0 Malathion (57.0% Tech.) |
| 12. | 18.0 Polyethylene Glycol |
|  | 2.0 Monamid S (Fatty amides) |
|  | 79.0 Powdered Fructose |
|  | 1.0 Malathion (57.0% Tech.) |
| 13. | 20.0 Shellac |
|  | 79.5 Sucrose |
|  | 0.5 Acephate (75.0% Tech.) |
| 14. | 14.0 Ethylcellulose |
|  | 6.0 Hydroxypropylcellulose |
|  | 79.5 Powdered Fructose |
|  | 0.5 Acephate (75.0% Tech.) |

TABLE 2-continued

| Example No. | Encapsulating Composition (Wt. %) |
| --- | --- |
| 15. | 50.0 Sterotex HM (fat) |
|  | 49.5 Sucrose |
|  | 0.5 Acephate (75.0% Tech.) |
| 16. | 18.0 Polyethylene Glycol |
|  | 2.0 Monamid S (Fatty Amides) |
|  | 79.5 Powdered Fructose |
|  | 0.5 Acephate (75.0% Tech.) |
| 17. | 14.0 Ethylcellulose |
|  | 6.0 Hydroxypropylcellulose |
|  | 79.9 Powdered Fructose |
|  | 0.1 Acephate (75.0% Tech.) |

Each particle was structurally sound, durable, and formed an eternal condensate of the diet component as well as the toxicant.

The diet/toxicant particles would be dispersed throughout a treatment area as a first type of bait particle in combination with discrete particles of a second type containing hydratable solids, which may or may not be the same as the diet component used in the diet/toxicant particles, in combination with a chemiluminescent agent in a second encapsulating agent. A relatively small number of light emitting particles is needed to attract moths. The moths are initially attracted to the light from the light emitting particles and, once in the area, sense and are attracted to the diet component. Thus, the hydratable solids component in the chemiluminescent particles is not desirably the same as the diet component but is, rather, a hydratable solid that performs the function of carrying the chemiluminescent agent thru the encapsulating material and into contact with oxygen where the reactions occur that are necessary to create luminescence.

We claim:

1. A bait useful for controlling lepidoptera populations, said bait being in the form of discrete particulates and comprising:
   (a) a diet component for lepidoptera;
   (b) a toxicant;
   (c) a chemiluminescent, visual attractant that produces light through one or more chemical reactions when brought into contact with oxygen from the permeation of moisture, wherein said attractant is present in an amount sufficient to emit light in darkness; and
   (d) an encapsulating agent that is solid at room temperature and which will swell when the humidity rises sufficiently to permit moisture to permeate said agent, provide oxygen to said visual attractant, hydrate said diet component and said toxicant, and form an external condensate of said diet component and said toxicant.

2. A bait according to claim 1 wherein said diet component is selected from the group consisting of honey, fructose, sucrose, glucose, corn syrup solids, and maltodextrin.

3. A bait according to claim 1 wherein said toxicant is selected from the group consisting of malathion, permethrin, cypermethrin, endosulfan, and acephate.

4. A bait according to claim 1 wherein said chemiluminescent, visual attractant comprises an oxygen-sensitive component and a salt that complexes with the oxidized byproducts of said oxygen-sensitive component to extend the duration and intensity of the chemiluminescence.

5. A bait according to claim 4 wherein said oxygen-sensitive component is selected from the group consisting of tetrakis (disubstituted amino) ethylene and tetrakis (dimethyl amino) ethylene.

6. A bait according to claim 4 wherein said salt is selected from the group consisting of lithium chloride, sodium nitrate, potassium nitrate, sodium carbonate, potassium carbonate, sodium thiosulfate, potassium thiosulfate, sodium phosphate, potassium phosphate, sodium borate, potassium sulfate, and potassium bromide.

7. A bait according to claim 1 wherein said bait is in the form of a discrete particle having a homogeneous dispersion of said diet component, said toxicant, and said chemiluminescent agent in an encapsulating matrix.

8. A bait according to claim 1 wherein said bait is in the form of a discrete particle having a core comprising said diet component, said toxicant, and said chemiluminescent agent and an outer shell of an encapsulating matrix.

9. A bait particle according to claim 1 wherein said diet and said toxicant are in a first bait particle in a first encapsulating agent, and said chemiluminescent, visual attractant is in a second bait particle in a second encapsulating agent.

10. A bait for controlling lepidoptera populations comprising a first bait particle consisting essentially of a diet component for lepidoptera and a toxicant in a first encapsulating agent that will permit moisture to permeate and form an external condensate of said diet component and said toxicant; and a second bait particle comprising hydratable solids and a chemiluminescent, visual attractant that is solid at room temperature, swells with moisture, and produces light through one or more chemical reactions when brought into contact with oxygen introduced from the permeation of moisture, wherein said attractant is present in an amount sufficient to emit light in darkness in a second encapsulating agent.

11. A bait according to claim 10 wherein said chemiluminescent, visual attractant comprises an oxygen-sensitive component and a salt that complexes with the oxidized byproducts of said oxygen-sensitive component to extend the duration and intensity of the chemiluminescence.

12. A bait according to claim 11 wherein said oxygen-sensitive component is selected from the group consisting of tetrakis (disubstituted amino) ethylene and tetrakis (dimethyl amino) ethylene.

13. A method for controlling lepidoptera populations by the step comprising:

distributing within a target area baits in the form of discrete particles and comprising:

(a) a diet component for lepidoptera;
(b) a toxicant;
(c) a chemiluminescent, visual attractant that produces light through one or more chemical reactions when brought into contact with oxygen from the permeation of moisture, wherein said attractant is present in an amount sufficient to emit light in darkness; and
(d) an encapsulating agent that is solid at room temperature and which will swell when the humidity rises sufficiently to permit moisture to permeate said agent, provide oxygen to said visual attractant, hydrate said diet component and said toxicant, and form an external condensate of said diet component and said toxicant.

14. A method according to claim 13 wherein said diet component is selected from the group consisting of honey, fructose, sucrose, glucose, corn syrup solids, and maltodextrin.

15. A method according to claim 13 wherein said chemiluminescent, visual attractant comprises an oxygen-sensitive component and a salt that complexes with the oxidized byproducts of said oxygen-sensitive component to extend the duration and intensity of the chemiluminescence.

16. A method according to claim 15 wherein said oxygen-sensitive component is selected from the group consisting of tetrakis (disubstituted amino) ethylene and tetrakis (dimethyl amino) ethylene.

17. A method according to claim 15 wherein said salt is selected from the group consisting of lithium chloride, sodium nitrate, potassium nitrate, sodium carbonate, potassium carbonate, sodium thiosulfate, potassium thiosulfate, sodium phosphate, potassium phosphate, sodium borate, potassium sulfate, and potassium bromide.

18. A method according to claim 13 wherein said bait is in the form of a discrete particle having a homogeneous dispersion of said diet component, said toxicant, and said chemiluminescent agent in an encapsulating matrix.

19. A method according to claim 13 wherein said bait is in the form of a discrete particle having a core comprising said diet component, said toxicant, and said chemiluminescent agent and an outer shell of an encapsulating matrix.

20. A method according to claim 13 wherein said diet and said toxicant are both in a first particle, and said chemiluminescent, visual attractant is in a second particle.

* * * * *